United States Patent [19]

Ohsumi et al.

[11] 4,219,844
[45] Aug. 26, 1980

[54] APPARATUS FOR DETECTING THE SURFACE FLAWS OF A RED-HEATED METAL PART

[75] Inventors: Atushi Ohsumi; Yoshinao Yamagishi; Kaoru Daigo, all of Fukuyama; Tomio Yamamoto, Takamatsu; Katsuya Yamada, Kawagoe, all of Japan

[73] Assignees: Nippon Kokan Kabushiki Kaisha, Tokyo; Fuji Toyuki Co., Ltd., Takamatsu; Katsuya Yamada, Kawagoe, all of Japan

[21] Appl. No.: 813,334

[22] Filed: Jul. 6, 1977

[30] Foreign Application Priority Data

Jul. 9, 1976 [JP] Japan .................................. 51-81784

[51] Int. Cl.² .............................................. H04N 7/18
[52] U.S. Cl. ..................................... 358/106; 358/101; 358/217
[58] Field of Search ............... 358/101, 106, 107, 108, 358/217, 113

[56] References Cited

U.S. PATENT DOCUMENTS

| | | | |
|---|---|---|---|
| 3,187,185 | 6/1965 | Milnes | 358/107 |
| 3,646,267 | 2/1972 | Tompsett | 358/217 |
| 4,118,732 | 10/1978 | Ichijima | 358/101 |
| 4,131,490 | 12/1978 | Oishi | 358/101 |

*Primary Examiner*—Howard W. Britton
*Attorney, Agent, or Firm*—Frishauf, Holtz, Goodman & Woodward

[57] ABSTRACT

An apparatus for detecting the surface flaws of a red-hot metal part includes a light source for illuminating a predetermined area on the surface of a moving red-hot metal part, an image pick-up device for picking-up the image on the metal part surface formed by the light rays from the light source, and a shutter disposed on the optical path between the light receiving surface of the pick-up device and the light source. The reflection energy from the metal part surface corresponding to the incident light rays from the light source is set up to be much larger than the radiation energy of the metal part per se. This relation of energy is set up by adjusting the illumination of the light source. The surface flaws are detected in such a manner that at least one of a series of video signals fed from the image pick-up device after the shutter release is selected as the optimum video signal for flaw detection, and properly selected.

4 Claims, 4 Drawing Figures

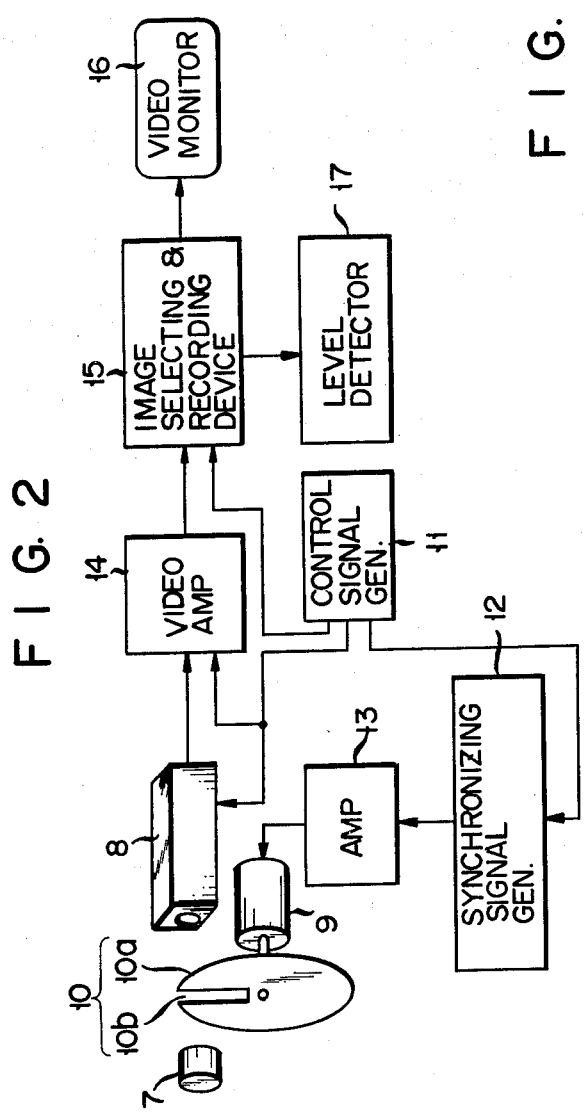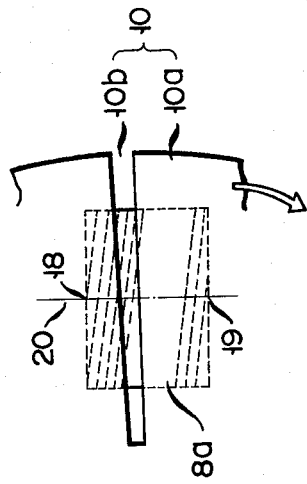

APPARATUS FOR DETECTING THE SURFACE FLAWS OF A RED-HEATED METAL PART

BACKGROUND OF THE INVENTION

The present invention relates to an apparatus for detecting the surface flaws of a red-hot (hereinafter red-heated) metal part.

The flaws on the surface of the metal part, such as a slab or bloom must be removed before the metal part is fed to the succeeding step. When the moving metal part in a red-hot heated condition has flaws on the surface, it is impossible to detect them by the naked eye in a normal surrounding illumination. Therefor, to detect the flaws on the red-hot heated metal part by the naked eye, the metal part must be cooled to be at a normal temperature condition. By contrast, if the flaw or its condition such as size or depth may be detected under the red-heated condition, the following many advantages may be enjoyed. By executing the flaw detection preceeding the hot scarfer immediately after the metal part is rolled, the necessary steps of the flaw removal for presence, size and position of the flaw may be taken for each steel part. This eliminates yield deterioration due to excessive application of the hot scarf and the need of another flaw removal work operation due to insufficient application of the hot scarf.

Further, the flaw detection is permitted immediately after cogging roll or the hot scarf is rolled. Accordingly, the flaws detected may be partly remedied by the hot rolling, with the metal part in its red-heated state. This permits the use of a direct rolling method in which the red-heated metal part is rolled by the rolling mill at the succeeding step not by way of the furnace and a hot metal part entering method in which the red-heated metal part enters the furnace. The thermal energy loss due to successive cooling and heating of the metal part is relieved. In this case, if the hot partial flow removal should be impossible, it is checked from the condition of the surface flaw of each metal steel part whether the use of the direct rolling method or the hot metal part entering method is proper or not. If the use of such method is improper, the metal part is transferred to the cooling and flaw removal process. On the other hand, if such is proper, the metal part is processed by the method of which the use is proper. In this way, the thermal energy loss may be allleviated also in this case.

SUMMARY OF THE INVENTION

Accordingly, an object of the present invention is to provide an apparatus for relatively simply and reliably detecting the surface flaws of a moving red-heated metal part.

According to the present invention, there is provided an apparatus for detecting surface flaws of a red-heated metal part comprising: a light source for iluminating a predetermined area on the surface of the red-heated metal part, the ilumination of which is so set up that the reflection energy from the metal part corresponding to the light rays from the light source is much larger than the radiation energy radiated from the metal part per se, an image pick-up device for picking-up an image of the metal part surface which is formed by the illumination from the light source and for generating video signals corresponding to the picked up image, a shutter disposed in the optical path between the light receiving surface of the pick-up device and the light source, and means for sampling a signal representing a surface flaw of the red-heated metal part from video signals obtained from the image pick-up device.

Other objects and features of the present invention will be apparent from the following description in connection with the accompanying drawings, in which:

BRIEF DESCRIPTION OF THE DRAWING

FIG. 2 is a block diagram of the FIG. 1 embodiment;

FIG. 3 illustrates the relation of the slit of a shutter to the light receiving surface of an image pick-up device.

DETAILED DESCRIPTION OF THE PREFERRED EMBODIMENTS

For observation of flaws on the surfaces of red-heated metal parts, for example, by an industrial television camera, the metal surfaces are irradiated by external light rays of which the energy is sufficiently larger than the irradiation energy of the metal per se, to form a shadow image of the metal part projected by the external light rays. In application of such a method to an actual production line, detection of presence, size and positions of flaws of the metal part as an object to be pictured must be under a condition that the metal part is moving. Otherwise, the production efficiency in the line will be considerably impaired. A moving metal part is photographed, for example, under the condition that a widely used vidicon tube, for example, is used for the pick-up device of the industrial television camera, with the usual scanning rate prescribed by the broadcasting standards. In this case, there is produced a "blur" on the picture due to the movement of the metal part. It is impossible thus that one attains a clear image of the object for the flaw detection. More specifically, when the red-heated metal part moving at a speed of 30 m/min. is pictured by using a television camera made under the Japanese broadcasting standards, the exposure time of the camera is 1/60 second so that the amount of the movement of the metal part over two continuous picture frames to be pictured reaches even 8 mm. Further, the pick-up tube used in the industrial television camera suffers more or less from residual image, with the result that the picture reproduced is a double or triple one. This is a serious problem in flaw detection.

Shortening the exposure time may lessen the residual image effect. An attempt to shorten the exposure time is to heighten the scanning rate of the television camera, i.e. the frame feeding rate. Increasing the frequency of the synchronous signal and widening the frequency band of the video amplifier are necessary for obtaining a sufficient scanning rate as well as a sufficient resolution. This is accompanied by economical and technical difficulties, and still with the adverse effect of the residual image.

To cope with this problem in the present invention, a mechanical shutter means is provided in front of a television camera, for example. The opening and shutting operation of the shutter is performed in synchronism with the read scanning signal of the television camera.

Such a construction introduces an instantaneous exposure.

Figure 1:
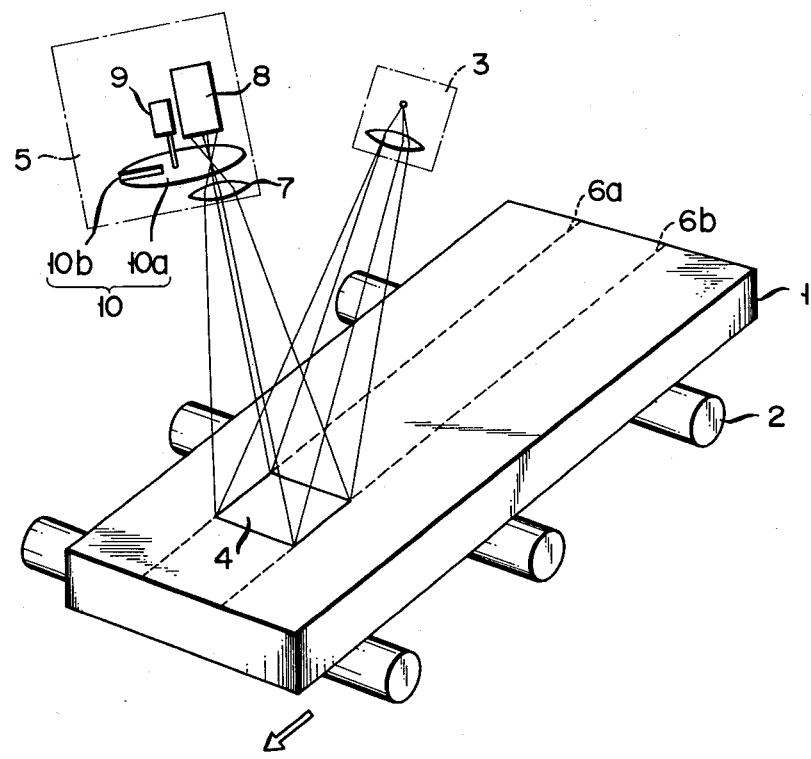
FIG. 1 shows a perspective view of a surface flaw detecting scheme of the invention.

The present invention will be described by using an embodiment thereof referring to the accompanying drawings. In FIG. 1, a red-heated metal part 1 such as a slab, bloom, or billet is moving over a table roller 2 in the direction indicated by an arrow. A light source 3 disposed above the red-heated metal part 1 illuminates a given area 4 on the red-heated metal part 1. The light intensity of the light source 3 must be so selected that the energy of the reflecting light from the metal part 1 is sufficiently larger than the radiation energy from the red-heated metal part 1 per se. A pick-up device 5 pictures a shadow image of the area 4 thus formed. Therefore, the flaw detection is made within the area defined by two phantom lines 6a and 6b extending in the moving direction of the metal part.

In a pick-up device 5, light rays emitted from the light source 3 are reflected from the illumination region 4 and the reflected light rays are imaged on the light receiving surface of a pick-up tube 8 via an optical lens 7. A mechanically operated shutter 10 which is rotatably driven by a motor 9 is disposed on the light path in front of the light receiving surface. The mechanically operated shutter 10 comprises a slit 10b formed in a rotating disc 10a. The light receiving surface of the pick-up tube 8 is exposed at the exposure time determined by the rotational speed of the disc 10a and the width of the slit 10b. Although not shown in FIG. 1, any means for removing oxide or dust on the surface of the metal plate by using high pressure water may be used, for the purpose of enhancing the detection accuracy of the surface flaws.

The picturing of the surface flaws of a red-heated metal part at more than 600° C. by an industrial television camera, may be physically interpreted in the following. All the materials radiate thermal energy depending on the temperature and the emissivity of the materials per se. In the case of a black body (emissivity=1), the amount of the radiation energy is given by the equation (1)

$$W \cdot d\lambda = \frac{c_1 \lambda^{-5}}{e^{c_2/\lambda T} - 1} \cdot d\lambda \quad (1)$$

where W: radiation energy (Watt/cm$^3$)
λ: wavelength (cm)
T: absolute temperature (°K)
$c_1$ and $c_2$: constant The red-heated condition of material indicates that the energy in a visual wavelength region (400 nm to 750 nm) in the radiation energy grows to be sensitive to the naked eye. Therefore, when one sees the red-heated material under external light rays, he actually sees the image which is a superposition of the shadow formed by illumination of external light rays onto the material and the image formed by the visual-wavelength regional energy radiated from material per se. Whether either of them dominates, depends on the ratio of them incident upon the naked eye. Let us consider the case, for example, where a steel piece at high temperature is observed under the illumination of 1,000 luxes by an incandescent lamp. When the steel part is at approximately 500° C., the amount of light rays of the steel part per se is weak and therefore the shadow formed by external light rays dominates in the image. When the steel part is at approximately 1,300° C., the radiation energy from the steel part per se is intensive and thus the shadow by external light rays becomes negligible.

Generally, in metal material, when it is heated to be at a high temperature, if the external light rays are correspondingly intensified, it must be that the shadow image by external light rays dominates as in the case of the low temperature case, although the total amount of light rays increases to dazzle one's eyes. Therefore, if a television camera, in place of the naked eye, is used to view such a metal part, it produces an output which is the product of the spectral sensitivity of the pick-up tube of the television camera and the shadow image by the external light and the radiation light rays of the metal material. Accordingly, one can observe an image predominantly including the shadow image by the external light rays.

The equation (1) shows that, in the red-heated material at less than 3,000° C., the amount of radiation light rays increases even in the visual light rays range as the wavelength of the radiation light elongates. To detect the flaws of the metal part, the shadow image by the external light rays is mainly observed, restricting the influence of the radiation light rays to be as small as possible. Therefore, it is necessary to use a filter blocking the passage of waves having long wavelength at the pick-up tube, to use a light source emitting light waves including mainly short wavelength components or further to use both the filter and the light source. Such an arrangement is effective to obtain a good shadow image with little amount of light rays.

A preparatory experiment was conducted on the basis of the above briefed theory. In the experiment, the red-heated steel part used was one having a surface temperature of 600° to 1,200° C. and the light source was three super high pressure mercury-arc lamps providing 110,000 luxes on the plane vertical to the optical axis. The illuminated surface was observed by the naked eye from the position off the optical axis of regular reflection. In this case, a light reduction filter was used at the observing positions requiring the use of it. The surface flaws such as cracks, or line like flaws, were clearly observed, through the naked eye observation. Other observations were carried out by using a pick-up tube (of which the photoconductive surface is made of $Sb_2S_3$) having a spectral sensitivity characteristic resembling the specific visual characteristic of a man, and a pick-up tube (having the photoconductive surface of CdSe) of which the sensitivity at the longer wavelength side than the specific visual characteristic is high, respectively. In both cases, the surface flaws on the steel part were clearly observed. A clear observation could be made in another observation using a filter for cutting light waves with the wavelengths of more than 550 nm, in addition to the above-mentioned tubes.

FIG. 2 illustrates the pick-up tube shown in FIG. 1 and associated circuit construction. The pick-up tube 8 includes the body proper, electrodes, deflection coils, control drive portions and the other necessary parts. A control signal generator 11 generates a control signal to make a scanning in the vertical or horizontal direction of the pick-up tube 8. The control signal is reformed to be a drive signal to drive a motor 9 through a synchronous signal generator 12 and an amplifier 13. The drive signal makes the motor 9 rotate at a given rotational speed related to the vertical and the horizontal scanning periods. Therefore, synchronization is made among the scanning speed and the scanning time of the pick-up tube 8 and the time that the slit 10b of the shutter 10 traverses the light receiving surface of the pick-up tube 8, which synchronization will be described later. Reference numeral 14 designates a video amplifier for amplifying a video signal fed from the pick-up tube 8. Reference numeral 15 designates an image selecting and recording device to selectively video-record the most suitable one from the picture signals repeatedly fed from the video amplifier 14. The output of the video selecting and recording device is fed to a video monitor 16 for monitoring the television picture and a level detector 17 for detecting the flaws.

FIG. 3 illustrates the relation of the receiving surface 8a of the pick-up tube 8 and the slit 10b. The slit 10b rotates clockwise as indicated by the arrow in the figure. By the rotation, the respective points on the receiving surface 8a are successively exposed at an instant of time determined by the width of the slit 10b and the rotational speed thereof. That is, a so-called instantaneous exposure is made onto the light receiving surface. At the same time, an electron beam scans the light receiving surface 8a from the starting point 18 to the final point 19 as indicated by dotted lines, to read the picture.

Figure 4:
FIGS. 4(A) to 4(F) illustrate the time relation among the shutter, the scanning on the light receiving surface of the pick-up device and the picture display on the video monitor.

FIG. 4 shows the time-relation of the scannings of the shutter 10 and the light receiving surface 8a and the picture display by the video monitor 16. FIG. 4(A) illustrates the electron beam scanning of the pick-up tube 8, by typifying the scanning on the central line 20 on the light receiving surface 8a. In FIG. 4(A), a bottom line u and a top line l correspond to the starting point 18 and the final point 19 of the scanning on the light receiving surface 8a in FIG. 3. The electron beam slopes upward from the bottom line u to the top line l is indicated by reference numeral 21, for reading the picture. The electron beam reading the top line l slopes downward to return to the bottom line, along a dotted line 22 (a vertical fly-back line). During this period, no reading operation is conducted. The repeat of this set of scanning operations picks up a complete picture on the receiving surface 8a. As shown in FIG. 4(A), the period of time represented by $t_F$ is the sum of the reading time and the vertical fly-back time $t_c$, representing a scanning period.

FIG. 4(B) illustrates how the slit 10b traverses the light receiving surface 8a, by typifying the traverses of it with respect to the central line 20. In this illustration, the bottom and top lines u and l are used correspondingly as in the FIG. 4(A) case. Although the shutter 10 circularly moves at a fixed angular velocity, the slit 10b moving on the central line 20 is assumed to travel at an approximately constant velocity. Therefore, the shutter 10 opens at a straight line 23 while it shuts at a line 24. Reference character $t_o$ represents the exposure time determined by the width of the slit 10b and the rotational speed of the shutter 10. Character $t_K$ represents the period that the slit 10b traverses the light receiving surface 8a. To obtain a good quality picture, it is necessary that the reading scanning and the exposure are time-related as shown in FIGS. 4(A) and 4(B). More precisely, the starting point and the final point are set on appropriate points m on the center line 20. The read scanning is completed at a point 25; the shutter opens at a point 26 and shuts at a point 27; the read scanning starts at a point 28. As a matter of course, it is necessary that the above condition must be true for the entire surface of the light receiving surface 8a including the central line 20. To this end, the above time relation must hold among read scanning point (i.e. inclination of the straight line 21), fly-back time $t_c$, moving velocity of the slit 10b (i.e. inclination of each straight line 23 and 24), and exposure time $t_o$ of the shutter exposure time. Further, the scanning of the pick-up tube must be synchronized with the time that the slit of the shutter passes the light receiving surface as mentioned above. The synchronization is realized by the synchronizing generator 11. In FIG. 3, the horizontal scanning lines are substantially in parallel with the slit. In order to obtain a high quality picture by making these in orthogonal relation, the exposure of the entire picture must be completed during the vertical fly-back period $t_c$.

Briefly, in the invention, the light receiving surface of the pick-up tube is instantaneously exposed during the time that no read scanning is carried out. The image of the object to be picked up is taken out in the form of an electrical signal in the subsequent read scanning. Incidentally, the image is stored on the light receiving surface. Therefore, the pick-up tube to be used must be of the type in which, after the light illumination on the tube is ceased, the video information included in the illuminated light is kept on the light receiving surface until the subsequent read scanning starts. However, such an image pick-up tube is accompanied by residual image phenomenon. Accordingly, the image stored on the light receiving surface remains after one time of the read scanning is completed and the same image information is produced at the second time of the read scanning operation, although the output of the pick-up tube reflecting the image information is so weak when it is read out. As a result, the image reproduced is a superposition of the preceding and succeeding images and therefore it is inconvenient for observation of a moving object. For this reason, the period $t_K$ of the shutter must be much larger than the read scanning period $t_F$ of the pick-up tube in order that the shutter is opened after the residual image is almost negligible in practical use, for ensuring a high quality picture. Generally, the residual image characteristic of the pick-up tube depends on the kind of tube used, the amount of the incident light and the scanning method of electron beams. Thus, the erasing period, or $t_K/t_F$, must be appropriately selected by taking this fact into account.

The description to follow is how the picture information signal read out as mentioned above is displayed on the video monitor 16. An image to be picked up which is assumed to be almost immovable at the exposure time $t_o$ shown in FIG. 4(B) is projected onto the light receiving surface. As shown in FIG. 4(C), the pick-up tube 8 successively reads the picture signals $A_1$, $A_2$, $A_3$, .... $A_n$ where the signals following the signal $A_2$ are residual image signals gradually reducing in the amplitude. Note here that the residual signal $A_n$ is negligible in the image reproduction since the period $t_K$ is properly selected. Then, the shutter is opened again. Another object image, i.e. the surface shadow image of the moving metal part 1 is scanned to produce an image signal $B_1$ and its residual images $B_2$, $B_3$, .... $B_n$. Similar reading scannings will be repeated hereinafter. The output signals of the video amplifier 14 shown in FIG. 2 correspond to those in FIG. 4(C). If these signals are directly visualized on the video monitor 16, the density and brightness of the reproduced image varies in each frame, i.e. each vertical scanning, although the reproduced images of the signals $A_1$ to $A_n$ and $B_1$ to $B_n$ resemble each other. Thus, such the pictures make it difficult to find flaws on the metal part by the naked eye. For avoiding this problem, a proposition is given in which each scanning picture signals $A_1$ and $B_1$ representing the first picture image after the shutter is released is visualized continuously n times on the monitor 16 during the period $t_K$. See FIG. 4(D).

To this end, the image selecting and recording device 15 is used and operates to select as the most appropriate signal to detect the flaws the picture signals $A_1$ and $B_1$ representing the first picture frame after the shutter is released, from the image signals successively delivered from the pick-up tube 8 via the video amplifier 14. The device 15 temporarily stores the signals $A_1$ and $B_1$ and rearranges these signals $A_1$, $B_1$ . . . as shown in FIG. 4(D). The image selecting and recording device 15 is comprised of a device capable of instantaneously storing and reproducing the video signals, such as one using a magnetic disc or image storing tube.

In this manner, the surface condition of the red-heated metal part 1 which is moving is screened as a static picture on the video monitor 16, making it possible to detect the surface flaws of the metal part 1. If necessary, the output signal of the image selecting and recording device 15 is once recorded by an image recording device such as a video tape recorder (VTR) and the frame feeding rate at the image reproduction is slower than that at the image recording or the feeding of the picture frame is stopped. In this manner, the flaws may be more precisely detected.

With respect to the contrast of the reproduced picture, the picture signal $A_1$ is good as compared with the residual image signals $A_2$, $A_3$, . . . $A_n$, provided that these signals are produced under the same exposure condition. The contrast is gradually deteriorated in the order of $A_1$, $A_2$, . . . $A_n$. In these video signals, the best one for flaw detection is not necessarily the video signal $A_1$. When the external incident light is too intensive, the residual image signal $A_2$ or other signals may frequently be more suitable for flaw detection, with a clear picture having wide tonal range. This may be interpreted in the following. In the photoconductive type image pick-up tube currently most widely used, most of the residual image phenomena is of the capacitive residual image so that the video output of the residual image exponentially decreases as the number of read scannings increases. If the incident light is too intensive, the white parts of the reproduced picture is saturated in the amplifier when the dynamic range of the video amplifier is not so wide, with the result that the white parts do not appear on the monitor screen. On the other hand, the residual image is obtained as a signal that the contrast of the picture is reduced. The contrast of the picture is more reduced as the video signals take place more frequently. This means that, even for the intensive light rays, if the residual image signal is properly selected, a high contrast picture is obtained without any special video amplifier.

The amount of incident light rays varies largely on the surface temperature of the red-heated metal part and the surface processing method, even if constant is the intensity of the light source, and the physical dimensions of the red-heated metal part the light source and the image pick-up device. For this reason, it is difficult to adjust the iris of the optical system in order that the optimum exposure is attained for the first frames $A_1$ and $B_1$. Further, excessive or insufficient exposures are locally produced on the same picture by uneven illumination by the light source or uneven reflection of light rays due to uneven surface of the metal part. This possibly causes the inconvenience resulting from saturation of the video amplifier. Therefore, one of the practical methods is that the amount of light rays more than the optimum one for the first picture frame is previously given; the most suitable one is selected from the second and further subsequent residual images for continuously screening it on the video monitor for the period $t_K$.

The case shown in FIG. 4(E) is that the residual image signals $A_2$ and $B_2$ corresponding to the second picture frame is selected as the most suitable video signal and the most suitable one selected is displayed on the video monitor. The operations to select the second picture frame or the further subsequent picture frame from n picture frames and to record it may be executed by the image selecting and recording device 15, as in much the same method for the first picture frame. The selection of the best picture frame may be made through exchanging the picture frames by an operator observing the picture produced or through an automatic control device provided therein to give the optimum contrast. More precisely, when the most bright position of the signal representing the brightness exceeds a predetermined one, the exposure is assumed to be excessive, while when it is below the predetermined one, the first picture frame at that time is assumed to be the optimum exposure picture frame. The recording and reproducing method as shown in FIG. 4(F) is effective and is a modification of the methods of FIGS. 4(D) and 4(E). This method which is a straightforward introduction from the conventional interlaced scanning, simultaneously records video signals, for example, $A_2$, $B_2$ . . . and $A_3$, $B_3$ . . . of two continuous picture frames properly selected from a group of picture frames consisting of the first, second, third and other frames. In reproduction, the interlaced scanning is employed: all the odd lines from top to bottom of the first frame (in this example, the second picture) are scanned first, skipping over the even lines; after this vertical scanning cycle, all the even lines of the second frame (in this case, the third picture) which were omitted in the previous scanning run are scanned from top to bottom. Therefore, one views a superposition of two continuous pictures. The advantage of this method resides in more precise selection of picture. That is, when the method is compared with the one to select only one picture from a group of pictures, it provides a picture of which the quality is neutral compared to those of the above pictures. Therefore, if the method is used in combination with the method in which a single picture is continuously repeated for its reproduction, the optimum picture may be more precisely and completely selected. Further, the optimum picture may be selected in a manner that the video signal from the image pick-up tube is once recorded in the video recording means such as VTR and then the optimum picture is selected form displaying. This is applicable for both the manual and automatic switching methods. In the automatic switching method, the signal generated by the synchronous signal generator also is video-recorded.

As described above, utilization of the residual image prevents excessive or insufficient exposure on the part or entire of the surface of the metal part due to variation of the illumination or the reflection factor thereon, thereby to provide a high quality picture with high gradation for flaw detection.

Further, the flaws on the metal part surface may be detected by electrically processing the video signal and not by the observation by the naked eye. For example, most of the flaw part on the picture reproduced as mentioned above is darker, compared to the other parts thereon. On the basis of this fact, if the signal representing the black parts of picture falls below a predetermined level, it is assumed that it includes the flaw information, and further if such a signal occupies the area of the picture which is wider than a predetermined one, it is assumed that the picture has a flaw or flaws. Alternately, if the optimum picture signal to be recorded and reproduced in the recording device 15 is inputted into an electronic computer for pattern recognition, the automatic flaw detection may be executed more precisely. The automatic flaw detection circuit 17 shown in FIG. 2 executes such a function.

A more concrete example of the invention will be given hereafter. A slab immediately after cogging rolled (100 to 500 mm in thickness, 650 to 1,950 mm in width, 3 to 15 mm in length) was used for the object to be picked up. This slab heated to have a surface temperature of 900° to 1,200° C. is transferred at the speed of 30 to 60 m/min., being carried on a transfer table. During the transfer, the flaw detection was made by using the above-mentioned apparatus. The light source was three projectors using 250 W high pressure mercury lamps disposed above the slab with a separation therebetween of approximately 3 m. This light source illuminates a 250×250 mm² area of the slab surface, with the illumination of about 110,000 luxes on the plane orthogonal to the optical axis. In order to shade a fine flaw extending in the rolling direction, the light source was disposed off the transfer table, and it illuminated the slab from the position where is normal to the rolling direction but at the angle of about 30° with respect to a vertical line onto to the slab illumination surface. A descaler using high pressure water was provided at a position close to the rolling mill, for removing secondary scales attached on the slab at and after the cogging roll, before the flaw detection. The image pick-up device was disposed 2 m right above the illumination surface of the slab, being enclosed by a cooling means for protecting it from intense heat emanated from the red-heated slab. The pick-up tube used was of the photoconductive type in which CdSe or PbO providing high sensitivity and responsibility is used for the photoconductive surface. The scanning was in accordance with the Japanese television broadcasting standards: the scanning lines was 525, the scanning period $t_F$ 1/60 sec. and the flyback period $t_c$ 5 to 8% of the period $t_F$. The shutter exposure time $t_o$ was 1/1200 sec. and the shutter release repetition period $t_K$ was 1/5 sec. A single slit of the disc was used. Therefore, the read scanning is performed 12 times per one time of shutter release. In order to clearly catch the flaws extending in the rolling direction, the camera is disposed so that the rolling direction is orthogonal to the horizontal scanning line. A magnetic sheet was used for the image selecting and recording device 15. The selection of the optimum frame from the frames of picture produced by 12 times scannings may be manually or automatically made by comparing the amplitude of the signal representing dark or white portions of the picture with a reference value.

Observation of the slab was conducted under the just-mentioned condition. Clearly detected ones were line-like flaws 0.5 mm in width×5 mm in length, cracks larger than the above, scaling-off flaws, and bite patterns of rolls immediately after recutting which are not flaws but indicate the distinction of the picture. Additionally, the output of the image selecting and recording device 15 was once recorded in the VTR and was reproduced at the reproduction rate of ½ to ⅓ of the recording rate. As a result, the flaw was more clearly and easily detected. Still another observation of the slab surface was conducted by disposing these devices at the output side of the hot scarfer or the shearing machine. The flaw detection was good as in the previous cases.

The experiments showed that when the amount of the exposure light is so selected that the second or third frames immediately after the shutter release is optimum, the picture obtained is most stable and has fine detail and good definition. The automatic flaw detecting method in which the dark portion in a frame is processed in computation and the flaw detecting method by the naked eye were compared in performance. It was found that the former sufficiently functions for the detection of relatively large flaws such as scaling-off or cracks.

In the other observation, the flaw detecting device is provided between the cogging mill and the hot scarfer. With such an arrangement, the flaw removal by the hot scarfer was conducted by taking account of the results of the observation of the surface of the slab immediately after being rolled. In other words, necessity, depth and position of the flaw removal was appropriately changed while the surface of the slab is observed. The result was to eliminate the yield deterioration due to improper operation of the hot scarf or insufficient flaw removal at the subsequent step.

From the foregoing description, it will be seen that the surface flaws of the moving red-heated metal part may be relatively simply and assuredly detected. If the flaw detecting apparatus of the invention is used, the flaw removal method by the hot scarf may be determined for each steel part, thereby to eliminate the trouble of the flaw removal at the subsequent step due to improper operation of the hot scarf. When the flaw detection of metal part is carried out immediately after it is rolled and the flaws detected are removed, realized are a direct rolling method in which the steel part enters the rolling machine at the next step not by way of the furnace, and a hot plate insertion method in which the hot plate is directly inserted into the furnace, resulting in considerable reduction of heat consumption. In addition to the cogging steel parts (slab, bloom, billet, coarse steel parts), the flaw detecting apparatus of the invention is applicable to continuous casting steel parts. The flaw detecting apparatus may also be used to execute hot surface flaw detection at the output side or during the rolling of or by the hot rolling machine such as an original plate rolling machine, hot strip mill, roll formed section rolling machine, bar rolling machine and tube rolling machine. In this case, this remarkably improves the product quality and the yield.

It will be understood that the invention is not limited to the above-mentioned embodiments. For example, any other suitable opto-electric converting device may be used in place of the pick-up tube. In the examples mentioned above, the shutter is provided in front of the light receiving surface of the pick-up tube; however, it may be placed at any point on the optical path between the pick-up tube and the light source. For example, it may be placed between the metal part and the light source if the light source is powerful. Other modifications of the disclosed embodiments will be apparent to the person skilled in the art without departing from the spirit and scope of the invention as defined by the appended claims.

What we claim is:

1. Apparatus for detecting surface flaws on a red-hot heated metal part, comprising:
   a light source for illuminating a predetermined area on the surface of a red-hot heated metal part with light rays such that the reflection energy from the red-hot heated metal part corresponding to the light rays from said light source is much larger than the radiation energy radiated from the red-hot heated metal part;
   an image pick-up device having a light receiving surface for picking-up an image of the illuminated surface area of the red-hot heated metal part, said image pick-up device generating video signals corresponding to the picked up image;
   shutter means disposed in the optical path between the light receiving surface of said image pick-up device and said light source; and
   means coupled to said image pick-up device for sampling a signal representing a surface flaw of the red-hot heated metal part from video signals obtained from said image pick-up device.

2. The apparatus according to claim 1, in which said shutter means includes a rotatable disc having a slit formed therein, and a motor rotatably driving said disc, said shutter means being open when the light rays to said light receiving surface of said image pick-up device are passed through said slit of said disc, and being closed when the light rays are interrupted by the non-slit portions of said disc.

3. The apparatus according to claim 2, in which said flaw signal sampling means includes a video amplifier for amplifying a video signal delivered from said pick-up device, an image selecting and recording device receiving the output signal from said video amplifier, a level detector for detecting the level of a flaw signal in the video signals, said level detector being connected with said image selecting and recording device, and a drive circuit for driving said motor to rotate said disc at a predetermined speed, by a synchronous signal of said video signal.

4. The apparatus according to claim 3, in which said flaw signal sampling means further includes a video monitor for continuously displaying the optimum picture recorded in said image selecting and recording apparatus during the period that the shutter is closed.

* * * * *